(12) United States Patent
Erler

(10) Patent No.: US 11,331,055 B2
(45) Date of Patent: May 17, 2022

(54) METHOD FOR REDUCING A FOCAL SPOT DISPLACEMENT IN AN X-RAY RADIATION SOURCE OF A COMPUTED TOMOGRAPHY APPARATUS, AND COMPUTED TOMOGRAPHY APPARATUS

(71) Applicant: Carl Zeiss Industrielle Messtechnik GmbH, Oberkochen (DE)

(72) Inventor: Marco Erler, Oberkochen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 16/571,113

(22) Filed: Sep. 14, 2019

(65) Prior Publication Data

US 2020/0085384 A1  Mar. 19, 2020

(30) Foreign Application Priority Data

Sep. 14, 2018  (DE) .................... 10 2018 215 724.3

(51) Int. Cl.
*A61B 6/03*  (2006.01)
*A61N 5/10*  (2006.01)

(52) U.S. Cl.
CPC .......... *A61B 6/032* (2013.01); *A61N 5/1001* (2013.01); *A61N 5/1049* (2013.01); *A61N 2005/1061* (2013.01)

(58) Field of Classification Search
CPC ......... A61B 6/032; A61B 6/40; A61B 6/4021; A61B 6/4028; A61B 6/482; A61N 5/1042;
(Continued)

(56) References Cited

U.S. PATENT DOCUMENTS 5,822,395 A * 10/1998 Schardt ................. H01J 35/147
378/137
6,411,677 B1  6/2002 Toth et al.
(Continued)

FOREIGN PATENT DOCUMENTS

DE  10301071 A1  7/2004
DE  102007043820 A1  4/2009
(Continued)

*Primary Examiner* — Anastasia Midkiff
(74) *Attorney, Agent, or Firm* — Falk Ewers; Ewers IP Law PLLC

(57) ABSTRACT

A computed tomography apparatus and a method for influencing a position of a focal spot in an x-ray radiation source having a centering device to center an electron beam and a focus are provided. The method includes positioning a reference object into a beam path of x-ray radiation between the x-ray radiation source and an x-ray radiation detector, the x-ray radiation detector having detector elements to generate an x-ray image, capturing an x-ray image of the reference object at different powers, reducing a focal spot displacement occurring at the different powers based on a comparison of the x-ray images captured at the different powers with one another, by setting at least one altered electric current to operate the centering device or the centering devices of the x-ray radiation source, and operating the computed tomography apparatus with the altered electric current, by which the focal spot displacement was reduced.

11 Claims, 3 Drawing Sheets

(58) Field of Classification Search
CPC .. A61N 5/1043; A61N 5/1048; A61N 5/1064; A61N 5/1065; A61N 5/1077; A61N 2005/1019; H01J 35/00; H01J 35/02; H01J 35/025; H01J 35/04; H01J 35/14; H01J 35/147; H01J 35/153
See application file for complete search history.

(56) References Cited

U.S. PATENT DOCUMENTS

| | | |
|---|---|---|
| 7,001,071 B2 | 2/2006 | Deuringer et al. |
| 8,173,952 B2 | 5/2012 | Erler |
| 2007/0274457 A1 | 11/2007 | Dunham et al. |
| 2012/0020450 A1* | 1/2012 | Jung .................. A61B 6/4021 378/4 |
| 2014/0254755 A1* | 9/2014 | Tsujino ................ H01J 35/147 378/62 |
| 2015/0023472 A1 | 1/2015 | Schmitt et al. |
| 2017/0287668 A1* | 10/2017 | Yanagisawa .......... H01J 35/045 |
| 2017/0318652 A1 | 11/2017 | Meiler et al. |
| 2018/0261420 A1 | 9/2018 | Holch et al. |

FOREIGN PATENT DOCUMENTS

| | | | | |
|---|---|---|---|---|
| DE | 102006032607 B4 | 8/2011 | | |
| DE | 102013107736 A1 | 1/2015 | | |
| DE | 102017203932 A1 | 9/2018 | | |
| EP | 3240011 A1 * | 11/2017 | ............... | H05G 1/52 |
| EP | 3240011 A1 | 11/2017 | | |
| JP | 2011005018 A * | 1/2011 | ............ | H05G 1/025 |
| JP | 2011005018 A | 1/2011 | | |

* cited by examiner

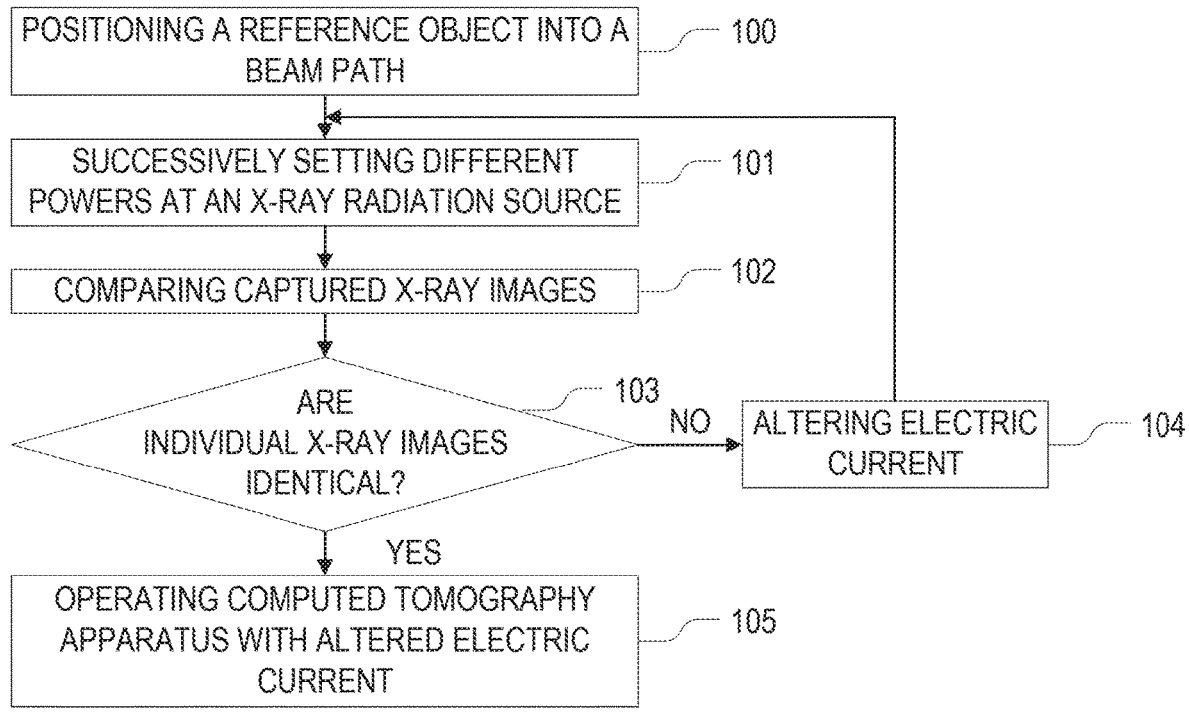
FIG. 3
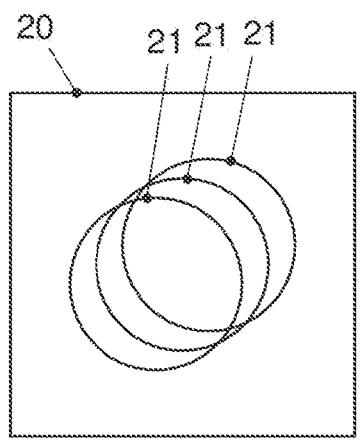  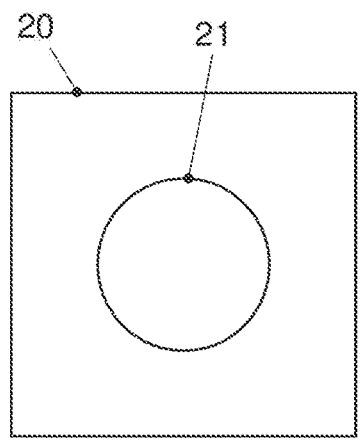
FIG. 2A  FIG. 2B

METHOD FOR REDUCING A FOCAL SPOT DISPLACEMENT IN AN X-RAY RADIATION SOURCE OF A COMPUTED TOMOGRAPHY APPARATUS, AND COMPUTED TOMOGRAPHY APPARATUS

CROSS REFERENCE TO RELATED APPLICATIONS

This application claims priority to German patent application DE 10 2018 215 724.3, filed Sep. 14, 2018, the entire content of which is incorporated herein by reference.

TECHNICAL FIELD

The disclosure relates to a method for influencing a position of a focal spot in an x-ray radiation source of a computed tomography apparatus, and to a computed tomography apparatus.

BACKGROUND

It is known that a computed tomography apparatus includes an x-ray radiation source, in which the x-ray radiation required for radiating through a measurement object is generated. The x-ray radiation source is often also referred to as a tube or x-ray tube. Typically, electrons are emitted from a filament serving as a cathode and are accelerated in the direction of an anode by an electric field generated by a high voltage. The accelerated electrons impinge on a focal spot of a target. The x-ray radiation arises in the region of the focal spot as a result of interaction with the target material.

Centering devices and focusing devices are known for influencing the electron beam in the x-ray radiation source. Known centering devices consist, e.g., of at least two coil pairs or pole pairs. The centering coils of each pair are arranged in particular on mutually opposite sides of an envisaged path of the electron beam in the x-ray tube. In the case of current flows through the coils of the coil pairs, the electron beam can be deflected. Such operation of the centering device(s) makes it possible to displace the direction of the electron beam in the plane (extending in the x-direction and y-direction) perpendicular to the electron beam. In particular, it is thereby possible to alter the position of the focal spot on the target. A focusing coil of a focusing device, which can be arranged in particular downstream of the centering coils along the current direction of the electrons, does not alter the location or the position of the electron beam on the target, but rather only defines the focus of the electron beam and thus influences just the shape and/or size of the focal spot on the target.

During operation of the x-ray radiation source, the electron beam in the x-ray radiation source proceeding from the filament generally does not coincide exactly with the optical axis of the beam guiding devices (in particular of the centering device(s) and the focusing device).

The optical axis at the focusing device coincides in particular with the direction of the electron beam if the electron beam passes centrally through the focusing device and perpendicularly to a plane of the focusing device. The image aberrations of the focusing device are then minimized. In particular, the optical axis proceeding from the filament, i.e., an emission site of the electrons of the electron beam, extends through the midpoint of the electromagnetic focusing device in the direction of the target.

Due to the beam guiding, the electron beam acquires a velocity component of a movement transversely with respect to the course of the optical axis. The effects of this differ in magnitude for different acceleration voltages (i.e., different forward velocities of the electrons). In general, this results in a lateral offset of the emission site of the electrons with respect to the optical axis and a non-vanishing angle of the path of the electron beam with respect to the optical axis. Due to the operation of a centering device, which is performed when an electric current flows through the centering device and which may be referred to as centering or deflection, the electron beam can be deflected such that it intersects the optical axis in a plane. For this purpose, the focal plane is generally chosen, i.e., the center of the magnetic focusing, with the result that image aberrations are thereby minimized. The center of the magnetic focusing is, in particular, the location where the center of a circular gap opening of an iron core of the focusing coil is arranged. The position of the focal spot on a stationary surface of the target cannot be kept constant within the power range of the x-ray radiation source in this way, however, since the electron beam furthermore has an intersection angle with respect to the optical axis. Different acceleration high voltages cause different intersection angles. Different input powers of the x-ray radiation source that result from the acceleration high voltages cause different convergence angles of the electron beam bundle. Both lead to a focal spot displacement.

By a centering by two centering devices, an electron beam not traveling on the optical axis can be aligned in such a way that it travels on the optical axis. A first centering by the first centering device can be performed such that the arbitrarily positioned and arbitrarily aligned electron beam passes through a defined point on the optical axis. The point at which the optical axis intersects a centering plane of the second centering device can be chosen as the defined point. The second centering by the second centering device then aligns the electron beam in such a way that the latter henceforth travels on the optical axis. Two centerings thus allow a correction of direction and position of an electron beam not traveling on the optical axis. In general, a centering is effected depending on a feedback signal with respect to a position of the electron beam on a plane perpendicular to the optical axis. Such a feedback signal can be for example a stop signal generated by deflection of the electron beam by the two centering devices with respect to a stop, from which stop signal information about a position of the electron beam in the centering plane of the first centering device and a position of the electron beam in a centering plane of the second centering device can be derived.

Since the target forms an oblique plane, a displacement in the y-direction is always coupled to a change in the magnification m. It is therefore sufficient to use a displacement in the y-direction since this results directly in a change in m. A displacement in the y-direction can be ascertained more simply and more accurately than a change in the magnification m. For adjusting the magnification m, it is therefore sufficient, in particular, to correspondingly adjust the focal spot in the y-direction.

In order to achieve imaging of the measurement object in the x-ray radiographs as accurately as possible and to reduce measurement errors, correspondingly accurate knowledge of the equipment geometry is required. This includes, in particular, knowledge about the position of the focal spot on the target. An inaccuracy in the position of the focal spot directly influences the measurement error since the inaccuracy also affects the positions in the radiograph. An inaccuracy of the positions in the radiograph subsequently results in errors during reconstruction. This effect is independent of the magnification and the resolution.

In particular, it can happen that the position of the focal spot changes over time. This can have a plurality of causes. Firstly, the filament (the cathode) can wear. This means that the location of the electron emission site at the filament does not remain constant for a relatively long period of time. Moreover, the location of the emission site very generally likewise changes if the filament is exchanged. In this case it is necessary to reset the centering devices of the x-ray radiation source. Furthermore, it may be the case that the alignment and/or arrangement of the beam guiding components are/is not as sought and/or have/has been altered.

It is known to perform a tube-internal adjustment of the focal spot position. In this case, an internal feedback signal of the x-ray radiation source is used to center the electron beam. Centering to a center of the focusing device (focus coil) is often effected in this case. However, the position of the focal spot is not determined in this case. This method is used in the context of a first initialization of the x-ray radiation source, e.g., after the production thereof or after a replacement of the filament. A tube-internal adjustment only makes possible a correction depending on a tube-inherent signal transmitter. Since the tube-inherent signal transmitter, embodied in particular as a stop, is not arranged in the focal spot plane but rather in a principal plane of the focusing device, this does not, however, make possible an optimum alignment of the electron beam relative to the totality consisting of centering device(s), focusing device and target. If a different power is set during subsequent operation of the x-ray radiation source, then a focal spot displacement can occur for the reasons described above, that is to say that the geometry during the capture of x-ray radiographs by the computed tomography apparatus changes. As a result, both the x-ray radiographs and the reconstructions of a measurement object that are generated therefrom can have additional aberrations that are avoidable by keeping the focal spot constant.

SUMMARY

It is an object of the disclosure to provide a method for influencing a position of a focal spot in an x-ray radiation source of a computed tomography apparatus, and a computed tomography apparatus, which make it possible to reduce a focal spot displacement that occurs during operation of the x-ray radiation source with different powersinput power settings.

According to an aspect of the disclosure, the focal spot displacement can be reduced by x-ray images of a reference object being compared with one another and at least one electric current flowing through a centering device being altered on the basis of the comparison. The position of the focal spot in the x-ray radiation source can therefore be kept approximately constant if the x-ray radiation source is operated at different input powers, i.e., in particular at a constant acceleration voltage and a changing current.

The disclosure is based on the insight that a focal spot displacement can be identified from x-ray images of the reference object. If the position of the focal spot on the target of the x-ray radiation source changes, then the captured x-ray image of the reference object also changes. This can be used to reduce, and in particular also to minimize, the focal spot displacement that occurs upon a change in the power of the x-ray radiation source. For this purpose, the reference object is arranged in a beam path between the target of the x-ray radiation source and an image detector of the computed tomography apparatus. For different input powers of the x-ray radiation source, in particular in each case at least one x-ray image of the reference object is captured by the detector. The x-ray images captured in this way are compared with one another. At least one current at at least one centering device of the x-ray radiation source is set or altered on the basis of the comparison.

One advantage of the disclosure is that the position of the focal spot is taken into account when centering the electron beam for the purpose of reducing the focal spot displacement. The centering is effected, in particular, by at least one electric current flowing through at least one centering device being altered. As a result of the reduction and in particular minimization of the focal spot displacement, the measurement conditions during the capture of x-ray images of a measurement object at different input powers of the x-ray radiation source can in turn be kept more constant. A measurement accuracy that is achievable in the reconstructions is increased as a result. The quality of a measurement of objects that is carried out by the computed tomography apparatus after a change in the input power of the x-ray radiation source is increased. Particularly in the case of dimensional measurements, that is to say measurements in which dimensions of a measurement object are intended to be determined, the accuracy of the measurement can be increased. This is advantageous in particular if the user wants to measure different workpieces at different input powers (e.g., different acceleration voltages) and to compare the measurement results.

The image detector is a detector that detects x-ray radiation in a spatially resolved manner. For this purpose, the detector has in a known manner, for example, a plurality of detector elements for generating an x-ray image, which are arranged next to one another, e.g., in rows and/or columns and which therefore generate image values (pixels) of an x-ray image during operation of the detector.

In particular, a method for influencing a position of a focal spot in an x-ray radiation source of a computed tomography apparatus is provided, wherein the x-ray radiation source has at least one centering device for centering an electron beam and an electromagnetic focusing device for focusing the electron beam, including the following steps:

(a) positioning a reference object into a beam path of x-ray radiation between the x-ray radiation source and an x-ray radiation detector of the computed tomography apparatus, wherein the x-ray radiation detector has a plurality of detector elements to generate an x-ray image, (b) capturing, by the x-ray radiation detector, at least one x-ray image of the reference object imaged onto the detector at different input powers by an x-ray radiation source having different input power settings, (c) reducing a focal spot displacement occurring at the different input powers of the x-ray radiation source based on a comparison of the at least one x-ray image captured at the different input powers with one another, by setting at least one altered electric current to operate the at least one centering device of the x-ray radiation source, and (d) reducing the focal spot displacement by operating the computed tomography apparatus at said at least one altered electric current for every input power of the multiple input powers of the x-ray source.

Furthermore, a computed tomography apparatus is provided which is configured in particular to carry out the method in any one of the configurations described. The computed tomography apparatus includes an x-ray radiation source having at least one centering device for centering an electron beam of the x-ray radiation source, an electromagnetic focusing device for focusing the electron beam, an x-ray radiation detector having a plurality of detector elements for generating an x-ray image, and a controller, wherein the controller is configured to process and to evaluate x-ray images of a reference object imaged onto the detector, said x-ray images being captured in each case at different input powers of the x-ray radiation source, to reduce a focal spot displacement of the x-ray radiation source on the basis of a comparison of the x-ray images captured at the different input powers with one another by setting at least one altered electric current for operating the centering device or the centering devices of the x-ray radiation source, and to use the altered electric current, by which the focal spot displacement was reduced, for operation of the computed tomography apparatus.

Ideally the electron beam in the x-ray radiation source travels on the optical axis and the focal spot is therefore not displaced if the power is changed. Ideally a comparison of the x-ray images captured at different input powers thus reveals that no deviation is present and the at least one electric current flowing through the centering device of the x-ray radiation source has been chosen well. However, if the electron beam does not travel on the optical axis, then the position of the focal spot is also displaced in the event of a change in power, which results in x-ray images deviating from one another in relation to the geometry of their generation. In particular, the image of the reference object in the x-ray images therefore changes in the event of a change in power. As a result of the comparison of the x-ray images, it is then established that the x-ray images differ from one another and a focal spot displacement is thus present. In order to reduce the focal spot displacement, the at least one electric current flowing through the centering device of the x-ray radiation source is then altered. Afterward, at the same input powers, x-ray images can once again be captured and the captured x-ray images can be compared with one another. As necessary, at least one electric current flowing through the centering device can be altered, which at least one electric current can be the same or a different current. This can optionally be repeated until the x-ray images, i.e., the images of the reference object, no longer differ from one another.

The comparison can be effected for example by a comparison of the individual image elements (pixels) of the x-ray images. If the x-ray images are identical, the respective pixels are also identical. This can be checked by a simple comparison of the image values of the respective pixels. In the case of two successively recorded x-ray images with the same geometry of focal spot, reference object, and detector, image differences can nevertheless occur. Therefore, for example, a maximum deviation of image values can be predefined which entails the decision still being taken that the same image value is involved. Moreover, a slight displacement of edges of the imaged reference object in the image can occur. Therefore, a maximum deviation of the position can be predefined which entails the decision still being taken that the same image is involved. Furthermore, a slight displacement of the focal spot can be acceptable and it is possible to predefine at least one corresponding maximum deviation in relation to image values and/or positions in the x-ray images of the reference object which entails no alteration of electric currents through the at least one centering device being carried out.

A two-dimensional object is typically chosen as the reference object, that is to say an object having a small extent in the dimension along which the imaging is effected (magnification direction). If the two-dimensional reference object consists only of a single substance (e.g., tungsten), the irradiation of the reference object with x-ray radiation substantially only results in two different intensity values in the imaging (projection) onto the detector or in the x-ray image captured thereby. One intensity value or image value corresponds to radiation being transmitted through material of the reference object and thus to an attenuation of the radiation. The other intensity value or image value corresponds to radiation passing through an opening or cutout of the reference object without being obstructed, or radiation traveling past the reference object without being obstructed. As a result, the imaging of the reference object can be identified particularly easily in an x-ray image since the contrast is high.

The reference object can be embodied for example as a film or thin layer composed of a material having the highest possible absorptance, for example in the form of a circular stop. Such a circular stop can be produced in a simple manner even for relatively large diameters, e.g., by laser drilling in the tungsten. To put it more generally, the film or thin layer composed of absorbent material has at least one opening and/or at least one cutout and is arranged in such a way that the x-ray image reveals the course of the edge of the opening and/or of the cutout.

In order to determine a position of the focal spot, a return value is required for all three spatial dimensions. In one simple case, this can be achieved by a circular shape (defined by the circle center having the coordinates x, and y, and the radius z).

By way of example, an imaging of a circular stop in the captured radiograph is evaluated for this purpose. For a sufficiently large or high-resolution circle imaging in the captured radiograph, a tangent can be ascertained for each region of the circumferential edge. Perpendicular to such a tangent, a position of the edge can then be determined or estimated by way of edge operators. By a plurality of edge positions determined in this way, a circle can be ascertained, which circle then corresponds to the circumferential edge of the circular stop. A circle fit is thus effected, for example by way of a minimization of a square deviation of the circle fit with respect to the plurality of edge positions. A position of a circle center and a circle radius of the circle imaging in the captured radiograph are obtained from the circle fit. By way of the known parameters of the geometric imaging in the computed tomography apparatus, it is possible to derive therefrom the position and the size of the focal spot. A change in the circle radius in two captured radiographs indicates a change in the focal spot, which brings about a change in the magnification, whereas a change in the circle center brings about a displacement in the detector coordinates.

Alternatively, it is also possible to carry out a reconstruction of the focal spot on the basis of the captured radiograph with the aid of the imaging of the circular stop. In this case, the determined circle center is used to extract edge profiles in the imaging symmetrically with respect to said circle center. Said edge profiles can have a variable, i.e., in particular asymmetrical, shape. If this is the case, a reconstruction of the focal spot likewise yields an asymmetrical shape and intensity distribution. A "mass centroid" is subsequently ascertained from said intensity distribution. A position of the "mass centroid" is subsequently used as an estimate for the position of the focal spot. In this way, a better estimate for the effective position of the focal spot than the position estimated from the circle fit by edge operators is afforded in this case.

The stop need not be positioned exactly at a predefined position in the computed tomography apparatus, but the reference object is typically imaged onto the detector with maximum possible magnification. This is explained on the basis of a simple example: A detector width DB and a distance SD between x-ray source and detector define an aperture angle alpha=2*arctan(2*SD/DB). A maximum magnification results from the ratio between the distance SD between the x-ray source and the detector and a distance SO between the x-ray source and the object as m=(SD/SO). On the basis of the intercept theorem, the magnification with a maximum possible object size can also be expressed as m=(DB/maximum object size), wherein this consideration assumes that the object is imaged onto the entire detector width. If m=150 and DB=400 millimeters (mm), then an object having a maximum object size of 2.66 mm can be imaged. By contrast, if the object (reference object) has a size of only 1 mm with the same set-up, it is imaged only onto 37.5% of the detector width. If a (pinhole) stop of this size is chosen as the reference object, then an unsharpness at the stop imaging must not exceed a radius of the (pinhole) stop. As a result, the maximum allowed/evaluatable stop imaging occupies 2*37.5%<100% of the detector width, since an unsharpness is always generated on both sides of an edge of the (pinhole) stop. In particular, a profile of the unsharpness represents a line spread function (LSF) in this spatial direction, from which an intensity distribution in the focal spot can be reconstructed. A circular (pinhole) stop having an aperture diameter of 1 mm is thus suitable.

Provision can be made for the reference object to be arranged in the computed tomography apparatus in a manner rotatable about a rotation axis (for example on a filter wheel), such that it can be rotated into the beam path of the computed tomography apparatus as necessary. After the method has been carried out, the reference object is removed again from the beam path of the computed tomography apparatus.

After the method has been carried out, it can be provided that once again for the same input powers in each case an x-ray image of the reference object is captured and, if appropriate, at least one current through the at least one centering device is altered.

An exemplary embodiment therefore provides for method steps (b) and (c) to be repeated for the same input powers of the x-ray radiation source. What can thereby be achieved, in particular, is that a focal spot displacement is not only reduced but also minimized. Particularly after the first performance of method step (b) or else after a repeated performance of this method step, it can also happen that at least one electric current through the at least one centering device is indeed altered, but the focal spot displacement is not reduced as a result. This can then be established upon a renewed performance of method step (b) and performance of the comparison of the captured x-ray images.

In particular, provision can be made here for the method steps to be repeated iteratively until the focal spot displacement is minimized.

The minimization can be established on the basis of a predefined criterion, for example, or the iteration of the method steps can be terminated when the criterion is satisfied. For example, the criterion may demand that the differences obtained from the comparison of the x-ray images captured at the different input powers do not exceed one predefined maximum value or a plurality of predefined maximum values. Apart from the maximum values for image values and positions of edges of the image of the reference object, as already mentioned above, statistical maximum values such as the standard deviation of all image values of two images to be compared are also suitable.

Provision can be made for the iteration of the method steps to be terminated if a specific threshold value, e.g., of a coefficient of measure is undershot, wherein the coefficient of measure represents a difference between the captured x-ray images. Such a coefficient of measure can be for example a number of different image elements (pixels) in the x-ray images.

In particular, it is possible to use known minimization algorithms during minimizing.

In an exemplary embodiment, it is provided that for reducing the focal spot displacement, a displacement of an image of the reference object in the x-ray images is determined by comparison of the x-ray images captured with different input powers. This is done by identifying the image or the imaging of the reference object, i.e., the imaged reference object, in the x-ray image, for example by pattern recognition methods. If the reference object is a pinhole stop having a circular hole, for example, then the edge of the hole will appear as substantially circular or elliptic in the x-ray image. The image can then be recognized and evaluated by application of a pattern recognition algorithm, e.g., by a controller of the computed tomography apparatus. By way of example, in each case the position of the circle center or intersection point of the semi-axes of the ellipse can be determined and used for determining the displacement. If the position of the focal spot in the x-ray radiation source changes in the event of a change in power, then the position of the imaged reference object in the captured x-ray image is also displaced. This displacement can then be ascertained from the individual positions that were determined for the imaging of the reference object in the x-ray images. By way of example, it is possible to determine a displacement vector or the absolute value thereof which describes this displacement. In particular, the procedure as described in this paragraph can be repeatedly carried out during the repetition of method steps (b) and (c).

With regard to the abovementioned check as to whether an iteration when capturing and comparing the x-ray images is to be terminated, the termination criterion can therefore consist, in particular, in the fact that a distinguished position resulting from the imaging of the reference object, in all the x-ray images of the reference object that are captured at the different input powers, does not differ more than by a predefined maximum value. The distinguished position can be not only the position of the center of the hole of a pinhole stop, but also some other position, such as, for example, the position of the area centroid mentioned below.

In an exemplary embodiment, it is provided that the displacement of the image of the reference object is determined on the basis of an ascertained area centroid of the image of the reference object in the x-ray images. The area centroid can be formed in a simple manner by determining a centroid of the imaging of the reference object. This is advantageous particularly in the case of non-circular, for example elliptic, images.

In an exemplary embodiment, it is provided that reducing the focal spot displacement in method step (c) is carried out on the basis of the determined displacement of the image of the reference object. By way of example, if a displacement vector is determined from a comparison of the positions of the images or images of the reference object in the x-ray images, then the displacement vector can serve as a basis for reducing and in particular minimizing the focal spot displacement. During the implementation of the method, the displacement vector is then reduced and in particular minimized by the at least one electric current flowing through the centering device of the x-ray radiation source being altered. In the case of minimization, the displacement vector or its absolute value can be used as a variable to be minimized or optimized. If the displacement vector or its absolute value is minimized, then the focal spot displacement in the x-ray radiation source is also minimized.

In an exemplary embodiment, it is provided that a focal spot displacement is calculated from the determined displacement of the image of the reference object, wherein reducing the focal spot displacement in method step (c) is carried out on the basis of the calculated focal spot displacement. For this purpose, a focal spot displacement is calculated from the image or the imaging of the reference object in the x-ray images by way of a known equipment geometry, that is to say the geometric arrangement of the x-ray radiation source and the focal spot, the course of the beam path, the reference object and the detector. The focal spot displacement is then reduced by the at least one electric current flowing through the centering device of the x-ray radiation source being altered. In the case of minimization, the focal spot displacement can be used as a variable to be minimized or optimized.

In a further exemplary embodiment, it is provided that the at least one electric current, altered for the purpose of the reducing, and flowing through the centering device of the x-ray radiation source is selected on the basis of an assignment of information, wherein the assignment of information represents an assignment of value pairs formed from an acceleration voltage and a cathode current of the x-ray radiation source to values for focal spot displacements depending on different currents flowing through the centering device of the x-ray radiation source and/or values for displacements of an image of the reference object in the x-ray images depending on different currents flowing through the centering device of the x-ray radiation source. By way of example, such an assignment can be implemented in the form of a look-up table. The assignment, for example in the form of the look-up table, has the advantage that for a determined displacement it is possible to estimate the extent to which the at least one electric current flowing through the centering device of the x-ray radiation source has to be altered at least tendentially. The reducing and also the minimizing can be accelerated in this way.

In order to create the assignment, in particular a look-up table, the reference object is positioned into the beam path and imaged onto the detector, wherein the at least one centering device, in particular the individual centering coil pairs thereof, are operated with different currents. This is effected for different acceleration voltages or electron energies. An x-ray image of the reference object is captured in each case by the detector. Since the electron beam is deflected to different extents in the x- and y-directions by the different currents flowing through the centering coil pairs, the position at which the electron beam impinges on the target and generates the focal spot is also displaced. In other words, the location of the focal spot is altered. This results in different x-ray images captured from the reference object. Said x-ray images can subsequently be evaluated in such a way that an assignment between the currents flowing through the centering coils and a displacement of the image or the imaging of the reference object in the x-ray image in the x- and y-directions is possible. From the displacement of the image of the reference object in the x-ray images, given known equipment geometry (exact positions of x-ray radiation source and/or focal spot, beam path, reference object and detector), the displacement of the focal spot can then be deduced or said displacement can be calculated therefrom.

If it is assumed, for example, that two coil pairs (with, in particular, a magnetic quadrupole having four currents for driving a total of four coils) are present, the following tables can be created for a cathode current by using different acceleration voltages and different electric currents flowing through the centering device of the x-ray radiation source and by determining the focal spot displacement in the x- and y-directions in each case for each combination. In the tables, the values of the focal spot displacement are indicated by A1 to A18 for the x-direction and by B1 to B18 for the y-direction:

At an acceleration voltage U1:

| | Centering coil 1 | | |
|---|---|---|---|
| Focal spot displacement | Current I1 | Current I3 | Current I5 |
| In the x-direction by | A1 μm | A3 μm | A5 μm |
| In the y-direction by | B1 μm | B3 μm | B5 μm |

Furthermore, at the acceleration voltage U1:

| | Centering coil 2 | | |
|---|---|---|---|
| Focal spot displacement | Current I2 | Current I4 | Current I6 |
| In the x-direction by | A2 μm | A4 μm | A6 μm |
| In the y-direction by | B2 μm | B4 μm | B6 μm |

Analogous tables result for the centering coils 3 and 4 with the currents I7 to I12.

At an acceleration voltage U2:

| | Centering coil 1 | | |
|---|---|---|---|
| Focal spot displacement | Current I13 | Current I15 | Current I17 |
| In the x-direction by | A13 μm | A15 μm | A17 μm |
| In the y-direction by | B13 μm | B15 μm | B17 μm |

Furthermore, at the acceleration voltage U2:

| | Centering coil 2 | | |
|---|---|---|---|
| Focal spot displacement | Current I14 | Current I16 | Current I18 |
| In the x-direction by | A14 μm | A16 μm | A18 μm |
| In the y-direction by | B14 μm | B16 μm | B18 μm |

Analogous tables result for the centering coils 3 and 4 with currents I19 to I24.

The step size of the different acceleration voltages in this case is 20 to 50 kV in an operating range of 80 to 250 kV.

On the basis of these tables, for each acceleration voltage in the abovementioned voltage range and for each coil pair, a focal spot displacement in μm/mA can then be calculated for each x-direction and each y-m-direction (m=magnification) and can be correspondingly assigned thereto, in particular stored in the look-up table.

The assignment, in particular the look-up table, is stored for example in a memory of the controller of the computed tomography apparatus, said memory being provided for this purpose.

In an exemplary embodiment, it is provided that the assignment of information is created before the focal spot displacement is reduced. In particular, by way of example, a look-up table can be generated before the focal spot displacement is reduced.

In an exemplary embodiment, it is provided that the at least one current, which is ascertained by the reducing, and which flows through the centering device of the x-ray radiation source, is defined in each case by the assignment of information for the value pairs composed of the acceleration voltage and the cathode current, and said value pairs being used for providing the different input powers. In particular, it can be provided that the at least one current flowing through the centering device of the x-ray radiation source, said at least one current being ascertained by reducing, for the value pairs composed of the acceleration voltage and the cathode current, said value pairs being used for providing the different input powers, is stored in each case in the look-up table. After the reducing, the ascertained currents for which the focal spot displacement is minimal are thus stored in the look-up table for the value pairs of acceleration voltage and cathode current on which the input powers used are based. This makes it possible, on the basis of an up-to-date measurement, to adapt the assignment, in particular the look-up table, and to bring it to an up-to-date status. The values for the at least one current flowing through the centering device of the x-ray radiation source can then be retrieved for corresponding acceleration voltages and cathode currents directly from the assignment, in particular from the look-up table, and be set at the at least one centering device.

In an exemplary embodiment, it is provided that the different input powers of the x-ray radiation source at a constant acceleration voltage are generated by differently chosen cathode currents. During the implementation of the method, the acceleration voltage is kept constant and only the cathode current is varied.

Alternatively, in one exemplary embodiment, it can be provided that the different input powers of the x-ray radiation source at a constant cathode current are generated by differently chosen acceleration voltages. In this case, the method is carried out at a constant cathode current, while different acceleration voltages are set.

In a further exemplary embodiment, it is provided that the different input powers of the x-ray radiation source are generated both by differently chosen acceleration voltages and by differently chosen cathode currents. What can be achieved in this way is that a complete correction is effected, such that the minimizing is effected depending both on the acceleration voltage and on the cathode currents.

In particular, it can be provided that at least in each case one x-ray image of the reference object imaged onto the detector is captured by the detector a first time at different input powers of the x-ray radiation source, specifically at a constant acceleration voltage and at different cathode currents in accordance with the different input powers. On the basis of a comparison of the x-ray images captured at the different input powers with one another, the focal spot displacement that occurs at the different input powers is reduced by setting at least one altered electric current for operating the centering device or the centering devices of the x-ray radiation source. This part of the method is then carried out a second time, but this time at a constant cathode current and at different acceleration voltages in accordance with the different input powers. The method is considerably shortened compared with a variation both of the cathode currents and of the acceleration voltages and setting of the electric currents by the centering device(s). Nevertheless, the focal spot displacement can be effectively minimized.

In a further exemplary embodiment, it is provided that the method is repeated at regular time intervals. Said time intervals can be chosen for example on the basis of a number of hours of operation of the x-ray radiation source. It can be provided that the time intervals are monitored by the controller of the computed tomography apparatus. A user then receives, as maintenance indications, for example, a message that minimizing the focal spot displacement is recommended. In this regard, it can be provided, for example, that such a maintenance indication is issued after 20 hours of operation of the x-ray radiation source.

Alternatively, it can also be provided that the time intervals are chosen on the basis of fixed time periods, for example depending on a few days, weeks or months.

Both when creating the assignment, in particular the look-up table, and when using the at least one electric current flowing through the centering device of the x-ray radiation source, said at least one electric current being found by the reducing, it can be provided that currents are calculated by interpolation and/or extrapolation for input powers other than those used during the process of creating the assignment, in particular look-up table, and/or the reducing. This is based on the experience that a focal spot displacement progresses linearly as the cathode current increases. By way of example, if a focal spot is ascertained at an electron beam power of 10 W and the focal spot is displaced by a specific absolute value at an electron beam power of 100 W, then it is possible to interpolate and/or extrapolate therefrom any value for a displacement for input powers between these two values and also for higher input powers.

BRIEF DESCRIPTION OF THE DRAWINGS

The disclosure will now be described with reference to the drawings wherein:

FIG. 2A shows a schematic illustration of three x-ray images of a reference object captured at different input powers before the process of reducing or minimizing a focal spot displacement;

FIG. 2B shows a schematic illustration of the three x-ray images of a reference object captured once again at the same input powers after the process of reducing or minimizing the focal spot displacement;

FIG. 3 shows a flow chart of a method for influencing a position of a focal spot in an x-ray radiation source of a computed tomography apparatus for reducing or minimizing a focal spot displacement according to an exemplary embodiment of the disclosure.

DESCRIPTION OF EXEMPLARY EMBODIMENTS

Figure 1:
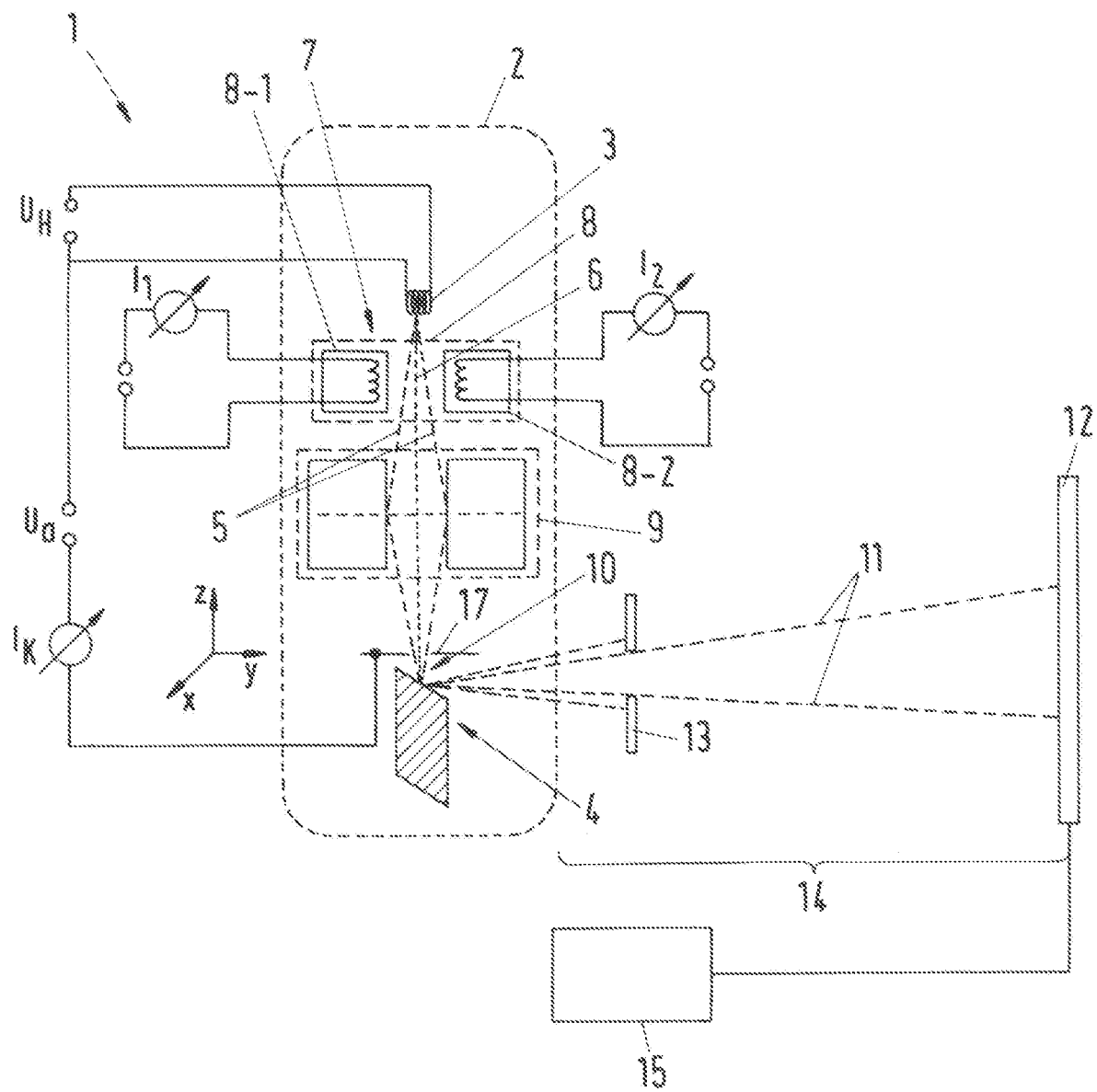
FIG. 1 shows a schematic illustration of a computed tomography apparatus according to an exemplary embodiment of the disclosure.

FIG. 1 shows a schematic illustration of a computed tomography apparatus 1 according to an exemplary embodiment. The computed tomography apparatus 1 includes an x-ray radiation source 2. The x-ray radiation source 2 includes a filament 3, which can be heated by a heating voltage $U_H$, such that electrons can thereby be emitted from the filament 3. The filament 3 forms a cathode. The electrons emitted from the filament 3 are accelerated in the direction of an anode (not shown) onto a target 4 with the aid of an acceleration voltage $U_a$. The emitted and accelerated electrons result in a cathode current $I_K$. The acceleration voltage $U_a$ and the cathode current $I_K$ result in the input power $P=U_a \cdot I_K$, with which the electrons impinge on the target 4.

The electrons form an electron beam 5, which ideally lies on an optical axis 6 of the x-ray radiation source 2. For shaping the electron beam 5, the x-ray radiation source 2 includes at least one centering device 7 having at least two coil pairs 8 (the second coil pair 8 is not shown for reasons of improved illustration; the coils of said second coil pair lie in front of and behind the plane of the figure in a manner rotated by +/−90° about the optical axis 6). The electron beam 5 can be displaced in the x-direction and the y-direction by the centering device 7, wherein the x-direction and the y-direction lie in a plane perpendicular to the optical axis 6. The coils 8-1, 8-2 of the coil pair 8 are operated with a current $I_1$ and $I_2$, respectively. Furthermore, the x-ray radiation source 2 includes a focusing device 9, which serves to displace a focus of the electron beam 5 along the optical axis 6 (z-direction).

In the exemplary embodiment shown in FIG. 1, a stop 17 is located in the beam path between the focusing device 9 and the target 4, said stop serving as an anode. For example, the stop 17 is a pinhole stop. The acceleration voltage Ua is present between the filament 3 and the stop 17. This means that the electron beam, after reaching the stop, is not accelerated further on its way to the target 4.

The electrons impinging on the target 4 generate x-ray radiation 11 in a focal spot 10 as a result of interaction with the target material, said x-ray radiation being imaged out of the x-ray radiation source 2 onto a detector 12 of the computed tomography apparatus 1. The detector 12 has a plurality of detector elements for generating an x-ray image.

In order to carry out the method for influencing a position of the focal spot 10 in order thereby to reduce, in particular to minimize, a focal spot displacement, a reference object 13, typically a thin circular pinhole stop, is arranged in a beam path 14 between the x-ray radiation source 2 and the detector 12.

The computed tomography apparatus 1 furthermore includes a controller 15, wherein the controller 15 is configured to process and to evaluate x-ray images of a reference object 13 imaged onto the detector 12, said x-ray images being captured in each case at different input powers of the x-ray radiation source 2, and to reduce a focal spot displacement of the x-ray radiation source 2 on the basis of a comparison of the x-ray images captured at the different input powers with one another by altering at least one electric current $I_1$ and $I_2$ flowing through the centering device 7 of the x-ray radiation source 2. Furthermore, the controller 15 is configured to use the altered electric current $I_1$ and $I_2$, by which the focal spot displacement was reduced, for operation of the computed tomography apparatus 1 at the corresponding input powers.

Typically, the x-ray radiation source 2 of the computed tomography apparatus 1 includes a further centering device (not shown), with the result that a complete centering of the electron beam 5 is possible. In the context of reducing a displacement of a focal spot position, the controller can then alter all currents $I_1$ and $I_2$ (and $I_i, \ldots, I_n$) present for operating the coils of the centering devices 7.

In the simplest case, the reducing can be effected by reducing, in particular minimizing, a deviation between the x-ray images captured at different input powers. This is illustrated schematically in FIGS. 2A and 2B. FIG. 2A shows superimposed x-ray images 20 that were captured from a circular stop as a reference object at different input powers. The respective image 21 of the reference object is shown in the x-ray images 20. For the reducing or minimizing, at least one of the electric currents $I_1$ and $I_2$ (FIG. 1) flowing through the centering device 7 of the x-ray radiation source 2 is altered. The x-ray images 20 captured at the same input powers after successful reducing or minimizing are shown in FIG. 2B. Ideally, the x-ray images 20 no longer differ from one another, and so the images 21 of the reference object are all congruent. After the reducing, in particular minimizing, it can be assumed that the focal spot displacement occurring at the input powers used is also reduced, in particular minimized.

FIG. 3 shows a schematic flow chart of the method for influencing a position of a focal spot in an x-ray radiation source of a computed tomography apparatus.

A first method step 100 involves positioning a reference object into a beam path of the computed tomography apparatus between a target of the x-ray radiation source and a detector of the computed tomography apparatus. The positioning can be effected for example by rotating a filter wheel arranged in the beam path to a position at which the reference object is located in the beam path.

The subsequent method step 101 involves successively setting different input powers at the x-ray radiation source, for example by a controller of the computed tomography apparatus. It can be provided, for example, that an acceleration voltage is altered at a constant cathode current. For each power set, an x-ray image of the reference object imaged onto the detector is captured by the detector.

For reducing the focal spot displacement, the captured x-ray images are compared with one another in method step 102. In method step 103, the x-ray images are checked in respect of their differences. By way of example, it is possible to check whether or not the image elements (pixels) of the individual x-ray images correspond to one another. If all the pixels are identical, then the comparison reveals that the focal spot displacement is minimized; in this case, the method continues with method step 105.

By contrast, if the x-ray images captured at different input powers differ from one another, then it may be assumed that the focal spot has also been displaced. In this case, the method continues with method step 104. In order to minimize the power-dependent focal spot displacement, at least one electric current flowing through the centering device of the x-ray radiation source is altered in method step 104. Afterward, the method is implemented once again starting from method step 101, that is to say that once again x-ray images are captured at the same input powers and are compared with one another and, if appropriate, the at least one electric current flowing through the at least one centering device is altered.

If, after the, in particular iterative, alteration of the at least one electric current flowing through the at least one centering device of the x-ray radiation source, a difference in the x-ray images can no longer be established, then the focal spot displacement is minimized and the method continues with method step 105.

Method step 105 involves using the value(s)—found after implementing the method—for the at least one current in each case at the associated input powers at the at least one centering device to operate the computed tomography apparatus.

It can also be provided that, in the context of the method steps 102 and 103, a displacement of the image, i.e., of the imaging, of the reference object in the x-ray images is determined and this displacement, for example in the form of a displacement vector derived therefrom, as minimization variable, is reduced, in particular minimized. By, in particular iteratively, altering the at least one electric current flowing through the centering device of the x-ray radiation source, and once again capturing x-ray images, the displacement vector is then reduced, in particular minimized.

It can furthermore also be provided that, in the context of the method steps 102 and 103, a displacement of the focal spot is calculated from a displacement of the image of the reference object in the x-ray images and the displacement of the focal spot is used as a minimization variable during the reducing, in particular minimizing. Given known equipment geometry, comprising in particular an arrangement and properties of the target in the x-ray radiation source, of the reference object and of the detector, the focal spot displacement can be calculated or estimated from the location and/or displacement of the image of the reference object in the captured x-ray images.

It can additionally be provided that a calibration of the equipment geometry (location and position of the detector and determination of the magnification) is carried out in a further optional method step. In this case, the calibration is carried out without the reference object arranged into the beam path.

Figure 4:
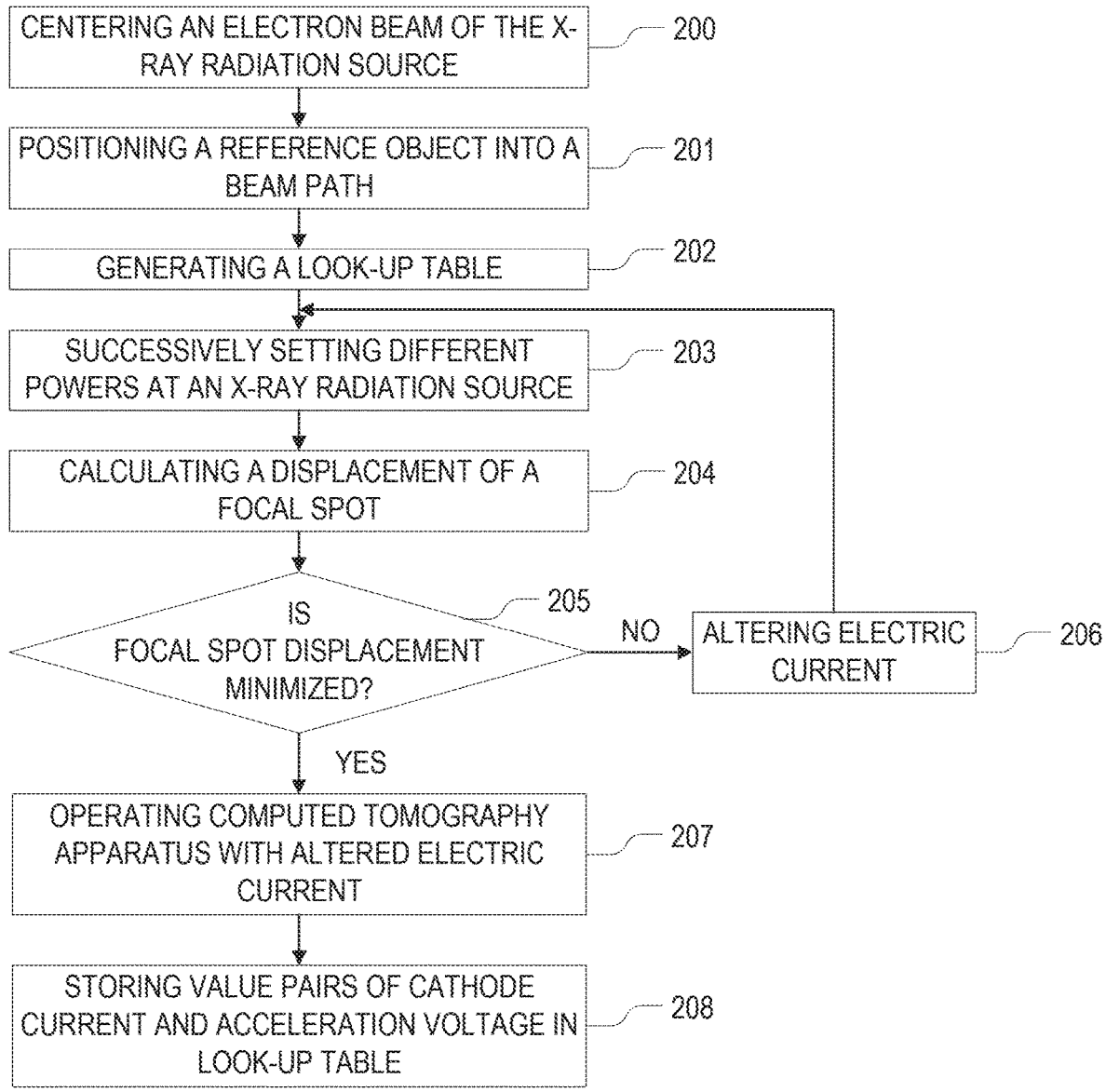
FIG. 4 shows a flow chart of a method for influencing a position of a focal spot in an x-ray radiation source of a computed tomography apparatus for reducing or minimizing a focal spot displacement according to another exemplary embodiment of the disclosure.

FIG. 4 shows a method for influencing a position of a focal spot in an x-ray radiation source of a computed tomography apparatus according to a further exemplary embodiment of the disclosure. Method step 200 involves centering an electron beam of the x-ray radiation source by a tube-internal centering. This method step 200 can be regarded as an initialization of the x-ray radiation source of the computed tomography apparatus.

Method step 201 involves positioning a reference object into a beam path of the computed tomography apparatus between a target of the x-ray radiation source and a detector of the computed tomography apparatus.

After the initializing, method step 202 involves generating a look-up table as assignment of information. In order to create the look-up table, the reference object positioned into the beam path is imaged onto the detector, wherein the at least one centering device, in particular the individual centering coil pairs thereof, are operated with different currents. This is effected for different acceleration voltages or electron energies. By the detector, an x-ray image of the reference object is captured in each case for different combinations of power (electron energy) and electric currents flowing through the centering device of the x-ray radiation source. The captured x-ray images are subsequently evaluated in such a way that an assignment between the electric currents flowing through the centering device of the x-ray radiation source and a displacement of the image of the reference object in the x-ray image in the x- and y-directions is possible. From the displacement of the image of the reference object in the x-ray images, given known equipment geometry (exact positions of x-ray radiation source and/or focal spot, beam path, reference object and detector), the displacement of the focal spot is then deduced, such that said displacement can be calculated therefrom. For the respective value pairs of cathode current and acceleration voltage, the focal spot displacement determined in each case is stored in the look-up table depending on the respectively used electric currents flowing through the centering device of the x-ray radiation source.

The subsequent method step 203 involves successively setting different input powers at the x-ray radiation source, for example by a controller of the computed tomography apparatus. For example, three input powers can be used: a standard power recommended by the manufacturer for operation of the computed tomography apparatus, and respectively a higher and a lower power. For each power set, an x-ray image of the reference object imaged onto the detector is captured by means of the detector.

Afterward, the focal spot displacement is minimized. This is effected on the basis of a comparison of the x-ray images captured at the different input powers. In this case, in method step 204, it is provided that a displacement of the focal spot is calculated from a displacement of the image, i.e., of the imaging, of the reference object in the x-ray images and the displacement of the focal spot is used as a minimization variable during the minimizing. Given known equipment geometry, including in particular an arrangement and properties of the target in the x-ray radiation source, of the reference object and of the detector, the focal spot displacement can be calculated or estimated from the location and/or displacement of the image of the reference object in the captured x-ray images.

Method step 205 involves checking whether the focal spot displacement is minimized. By way of example, it is possible to check whether the focal spot displacement lies below a specific threshold value. In the context of the checking, it is also possible to check whether or not the focal spot displacement converges across already effected iterations as a result of the measure of method step 206.

If the threshold value has not yet been undershot, then in method step 206 at least one electric current of the x-ray radiation source flowing through the centering device of the x-ray radiation source is altered and the method subsequently continues with method step 203. In particular, it is provided that altering the at least one electric current flowing through the centering device of the x-ray radiation source is effected on the basis of the look-up table created in method step 201. For this purpose, the altered currents are selected on the basis of the look-up table.

By contrast, if the threshold value is undershot, then the method continues with method step 207. Method step 207 involves using the values—altered after implementation of the method—for the at least one electric current flowing through the centering device of the x-ray radiation source in each case at the corresponding different input powers of the x-ray radiation source at the at least one centering device.

In particular, in an optional method step 208, it can be provided that the altered values for the corresponding value pairs of cathode current and acceleration voltage for the input powers used during the reducing or minimizing are stored in the look-up table, such that these can be directly retrieved during a subsequent measurement by means of the computed tomography apparatus. As a result, during subsequent measurements that use the same input powers, it is possible to dispense with carrying out the described method anew.

In particular, the corresponding entries in the look-up table can be correspondingly marked, such that it is possible directly to interrogate for which input powers a minimization of the focal spot displacement has already been carried out.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Computed tomography apparatus
2 X-ray radiation source
3 Filament
4 Target
5 Electron beam
6 Optical axis
7 Centering device
8 Coil pair
8-1 Coil
8-2 Coil
9 Focusing device
10 Focal spot
11 X-ray radiation
12 Detector
13 Reference object
14 Beam path
15 Controller
17 Stop
20 X-ray image
21 Image of the reference object
100-105 Method steps
200-208 Method steps
$I_1$ Current
$I_2$ Current
$U_a$ Acceleration voltage
$I_K$ Cathode current
$U_H$ Heating voltage

What is claimed is:

1. A method for reducing a focal spot displacement in an x-ray radiation source of a computed tomography apparatus, the x-ray radiation source having at least one centering device to center an electron beam and an electromagnetic focusing device to focus the electron beam, the method comprising the steps of:
   (a) positioning a reference object into a beam path of x-ray radiation between the x-ray radiation source and an x-ray radiation detector of the computed tomography apparatus, the x-ray radiation detector having a plurality of detector elements to generate x-ray images;
   (b) capturing, by the x-ray radiation detector, the x-ray images of the reference object imaged onto the x-ray radiation detector at different input powers by an x-ray radiation source having different input power settings;
   (c) reducing the focal spot displacement occurring at the different input powers of the x-ray radiation source based on a comparison of the x-ray images captured at the different input powers with one another, by setting a single altered electric current to operate the at least one centering device of the x-ray radiation source; and
   (d) reducing the focal spot displacement by operating the computed tomography apparatus at said single altered electric current for every input power of the multiple input powers of the x-ray source.

2. The method as claimed in claim 1, further comprising: repeating steps (b) and (c) for same input powers of the x-ray radiation source.

3. The method as claimed in claim 1, further comprising: determining a displacement of at least one x-ray image in the x-ray images of the reference object for the reducing of the focal spot displacement by comparing the x-ray images captured with the different input powers.

4. The method as claimed in claim 3, further comprising: determining the displacement of the at least one x-ray image of the reference object based on an ascertained area centroid of the at least one x-ray image of the reference object in the at least one x-ray image.

5. The method as claimed in claim 3, further comprising: the reducing of the focal spot displacement in step (c) being based on the displacement of the at least one x-ray image of the reference object.

6. The method as claimed in claim 3, further comprising: calculating the focal spot displacement from the displacement of the at least one x-ray image of the reference object; and
the reducing of the focal spot displacement in step (c) being based on the focal spot displacement calculated from the displacement of the at least one x-ray image of the reference object.

7. The method as claimed in claim 1, further comprising: selecting the at least one altered electric current flowing through the at least one centering device of the x-ray radiation source based on an assignment of information; the assignment of information representing an assignment of value pairs formed from an acceleration voltage and a cathode current of the x-ray radiation source to values for the focal spot displacement depending on different currents flowing through the at least one centering device of the x-ray radiation source and/or values for displacements of the at least one x-ray image of the reference object in the x-ray images depending on the different currents flowing through the at least one centering device of the x-ray radiation source.

8. The method as claimed in claim 7, further comprising: creating the assignment of information before the reducing of the focal spot displacement.

9. The method as claimed in claim 7, further comprising: setting the at least one altered electric current flowing through the at least one centering device of the x-ray radiation source for the value pairs formed from the acceleration voltage and the cathode current by the assignment of information, the value pairs being used to provide the different input powers, and the at least one altered electric current being ascertained by the reducing of the focal spot displacement.

10. The method as claimed in claim 1, further comprising: generating the different input powers of the x-ray radiation source both by selecting different acceleration voltages and by selecting different cathode currents.

11. A computed tomography apparatus, comprising:
an x-ray radiation source having at least one centering device to center an electron beam of the x-ray radiation source;
an electromagnetic focusing device to focus the electron beam;
an x-ray radiation detector having a plurality of detector elements to generate x-ray images, and
a controller configured to:
process and evaluate the x-ray images of a reference object imaged onto the x-ray radiation detector, the x-ray images being captured at different input powers of the x-ray radiation source;
reduce a focal spot displacement of the x-ray radiation source based on a comparison of the x-ray images captured at the different input powers with one another by setting a single altered electric current to operate the at least one centering device of the x-ray radiation source, and reduce the focal spot displacement by operating the computed tomography apparatus at said single altered electric current for every input power of the multiple input powers of the x-ray source.

* * * * *